US007638100B2

(12) United States Patent
Dawes

(10) Patent No.: US 7,638,100 B2
(45) Date of Patent: Dec. 29, 2009

(54) PLATELET INCUBATOR

(75) Inventor: Dennis K. Dawes, Indianapolis, IN (US)

(73) Assignee: Helmer, Inc., Noblesville, IN (US)

( * ) Notice: Subject to any disclaimer, the term of this patent is extended or adjusted under 35 U.S.C. 154(b) by 205 days.

(21) Appl. No.: 10/979,391

(22) Filed: Nov. 2, 2004

(65) Prior Publication Data

US 2006/0093514 A1  May 4, 2006

(51) Int. Cl.
*B01L 9/00* (2006.01)

(52) U.S. Cl. .................. 422/104; 422/99; 422/102; 221/105 R; 221/150 A; 221/150 HC

(58) Field of Classification Search .................. 422/62, 422/67, 99, 102, 104; 436/43, 46, 50; 221/9, 221/135, 150 R, 150 A, 150 HC; 435/286.1, 435/307.1, 309.1; 312/35, 42, 50
See application file for complete search history.

(56) References Cited

U.S. PATENT DOCUMENTS

| 5,409,312 | A | * | 4/1995 | Fletcher | 366/208 |
| 5,735,587 | A | * | 4/1998 | Malin et al. | 312/305 |
| 6,129,428 | A | * | 10/2000 | Helwig et al. | 312/114 |
| 6,274,374 | B1 | * | 8/2001 | Astle | 435/287.3 |
| 6,475,776 | B1 | * | 11/2002 | Higuchi | 435/303.3 |
| 6,489,168 | B1 | * | 12/2002 | Wang et al. | 436/37 |
| 6,536,859 | B1 | * | 3/2003 | Bathe | 312/305 |
| 6,568,770 | B2 | * | 5/2003 | Gonska et al. | 312/9.12 |
| 6,752,479 | B2 | * | 6/2004 | Ferger et al. | 312/350 |
| 2004/0115101 | A1 | * | 6/2004 | Malin | 422/104 |

OTHER PUBLICATIONS

Helmer, *Platelet Storage Systems*, twelve pages, published Jun. 2004.

\* cited by examiner

*Primary Examiner*—Jill Warden
*Assistant Examiner*—Dwayne K Handy
(74) *Attorney, Agent, or Firm*—Barnes & Thornburg LLP

(57) ABSTRACT

An incubator for storing blood platelets is provided. The incubator has a temperature controlled storage compartment and an apparatus for monitoring temperature within the storage compartment and other events. The incubator is configured to accept agitators within the storage compartment, the agitators operable to provide constant agitation of materials stored thereon. The information monitored is stored for access through a user interface or by an independent computer.

20 Claims, 11 Drawing Sheets

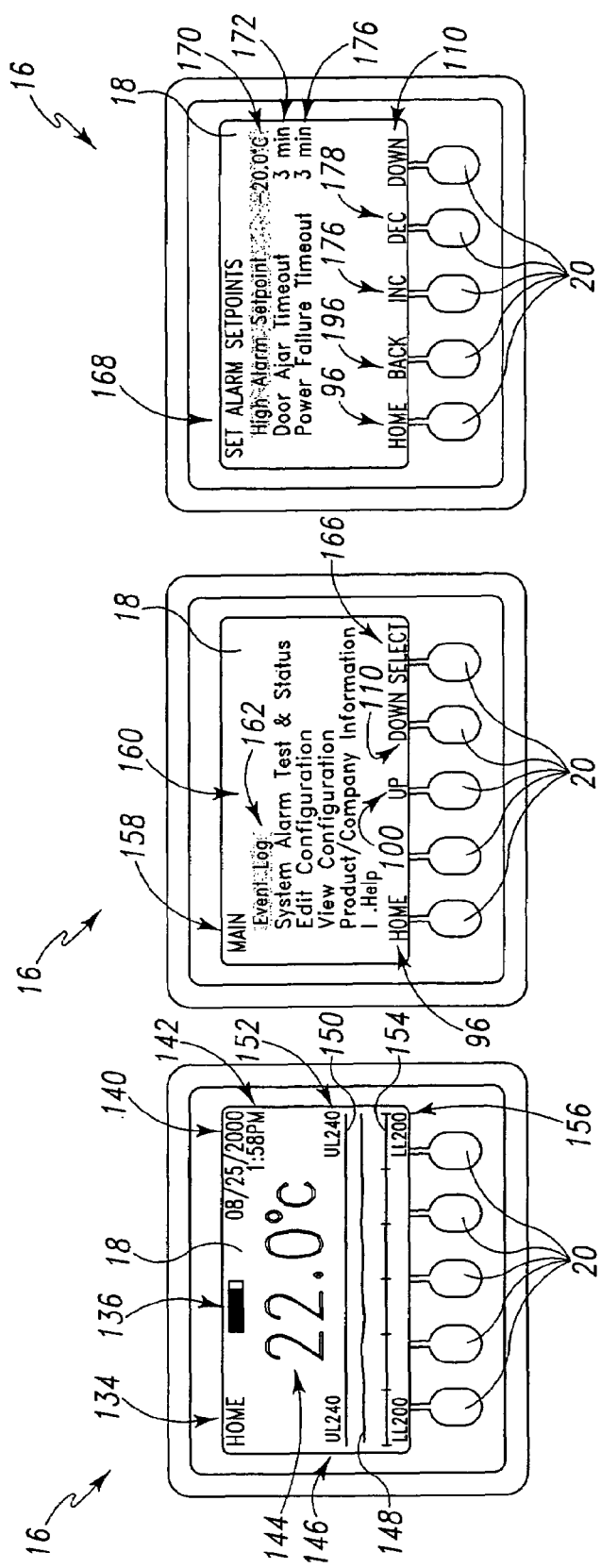

PLATELET INCUBATOR

BACKGROUND

The present invention is a platelet incubator. More specifically, the present invention is a platelet incubator having a platelet agitator and a central monitor and alarm system.

Platelets are one of several products yielded from whole blood and used in the medical field. Typically, platelets have a storage life of five days. For best quality, platelets must be stored in a closely controlled environment with minimal exposure to temperature variation. A closed environmentally controlled storage environment is often used. Incubation apparatuses typically have a temperature monitoring system which tracks the temperature in the storage compartment of a platelet incubator. This monitoring is accomplished through the use of a laboratory type, temperature chart recorder. Users of such equipment review the temperature chart to determine if the platelets were properly stored.

Additionally, it has been found advantageous to agitate the stored platelets to maintain the suspension of the platelets in the storage media. This agitation is accomplished through oscillation of the trays, drawers, or compartments used for storage of the platelets. Lack of oscillation may result in reduced yield of platelets or a reduced acceptable storage life.

SUMMARY

An incubator for blood platelets having alarms and an event log is provided. The incubator may have a cabinet with an opening to a storage compartment and a door pivotably coupled to the cabinet and closeable to cover the opening. The storage compartment may be configured to receive at least one agitator operable to agitate the platelets stored in the incubator. The incubator may also have a temperature sensor coupled to the cabinet in the storage compartment, a controller electrically coupled to the temperature sensor and operable to receive signals from the temperature sensor, and a user interface electrically connected to the controller configured to transmit and receive signals from the controller. The incubator may include additional temperature sensors with the controller receiving and processing signals from all of the sensors.

A refrigeration compressor unit may be located in the storage compartment and configured to continuously operate to reduce moisture and cool the air in the storage compartment. A temperature sensor may be located on the refrigeration compressor to monitor the temperature of the refrigeration compressor and the sensor may communicate the temperature to the controller. One or more fans may be present in the storage compartment to continuously circulate the air within the storage compartment so as to maintain a consistent air temperature throughout. A heating element may be located within the storage compartment and in communication with the controller such that the controller may control the heating element to maintain a constant temperature in the compartment. The controller may employ a proportional-plus-integral-plus-derivative (PID) based control methodology in controlling the heating element. In some embodiments, other feedback control methodologies may be used to control the heating element and manage the temperature in the storage cabinet. The heating element may have a thermal protection device to prevent an over-temperature situation by reducing or preventing electrical current flow to the heating element.

The agitator may have a base and a frame above the base, the frame configured to move laterally relative to the base. The base may include an electrical motor having an output shaft providing rotational output coupled to the base with an arm pivotably coupled to the motor and configured to translate the rotational output to linear output. The arm may be connected to the frame such that rotation of the motor results in lateral motion of the agitator frame relative to the base. The frame may be mounted on linear slides to facilitate the lateral motion between the frame and the base. A switch may be mounted to one side of the base and configured to sense the frame when the frame is near that side of the base. The controller may be operable to process the signal from the switch to determine the speed of motion between the frame and base. The switch may be a Hall effect proximity switch. In some embodiments, the switch may be an optical switch. In other embodiments, the switch may be a reed switch.

The door handle may engage a latch connected to the cabinet and the latch may include an electrical switch which is activated when the door is closed. In some embodiments, the electrical switch may be independent from the latch, coupled directly to the cabinet, and operable to sense that the door is closed. The electrical switch may be in communication with the controller to provide a signal that the door is closed.

The controller may simultaneously monitor and control the operating parameters of the incubator and agitator. The controller may be configured to control and monitor the incubator individually or the incubator and at least one agitator. In some embodiments, the controller may be configured to control and monitor multiple agitators located within the incubator.

The controller may have a microprocessor and a memory device. Additionally, the controller may include software stored in the memory device and operable to perform operations on the information received by the microprocessor to determine outputs to be provided by the microprocessor. The microprocessor may have a real time clock which maintains the information related to the current date and time. The controller may monitor main power, battery charge status, refrigeration compressor temperature, storage compartment temperature, agitator operation, and door status.

The controller may be operable to store data related to the monitored operations. For example, the controller may store the beginning and end of alarms for the door open, high storage compartment temperature, low storage compartment temperature, high refrigeration compressor temperature, low battery, no battery, mains power failure, and agitator failure. Storage of this event data may include a sequential event number, the alarm status such as beginning or ending, the alarm type, the date of the event, the time of the event, and the temperature in the storage compartment at the time the event occurred.

The log of event data may be accessible from the user interface in the form of displayed data. The log of event data may also be accessible through a peripheral connector configured to allow the memory stored by the controller to be accessed by an discrete computer.

The user interface may include a display screen and several user input devices such as buttons. The display may be a liquid crystal display (LCD). The user interface may be operable to display information output to the display by the controller and to provide inputs to the controller by way of the user input devices. The standard information displayed may include the temperature sensed by the temperature sensor, the current date and time, and a graphical representation of the temperature sensed for the previous 24 hours. The graphical representation of the temperature for the previous 24 hours may include lines representing the upper and lower control limits for the temperature.

The user interface may provide access to additional information beyond the standard information displayed. The display may operate as a menu driven device accessing various information stored within the controller. A main page may provide access to the event log, system alarms test and status, a view of the system configuration, a page to allow editing of the system configuration, product information, or a help index. A monitor screen may provide information as to the number of cycles completed by each agitator in the incubator. Some screens may require a password or pass code for a user to access the information.

The user interface may include input devices such as buttons. The input devices may be in communication with the controller and operable to change operating parameters of the incubator. The input devices may be operable to navigate the various menus and screens in the display. In some embodiments, the input devices may be membrane switches. In other embodiments, the input devices may be integrated in the display with the display being a touchscreen device. The display may be a monochromatic display. In some embodiments, the display may be a colored display.

The incubator may further include a sound output device to provide various audible alerts to a user. The sound output device may be connected to the controller and operable to receive a signal from the controller. The sound output device may be operable to emit various tones, tone patterns, and volumes based on inputs from the user. In some embodiments, the sound output device may be a speaker. In some other embodiments, the sound output device may be a piezoelectric device. In some embodiments, the sound output device may be coupled to the display. In other embodiments, the sound output device may be coupled to the cabinet. In some embodiments, multiple sound output devices may be used.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which:

FIG. 5 is a perspective view of a user interface of the platelet storage system of FIG. 1, the user interface having a display screen displaying a home page;

FIG. 6 is a perspective view of the user interface of FIG. 5, the display screen displaying a main screen;

FIG. 7 is a perspective view of the user interface of FIG. 5, the display screen displaying a set alarms screen;

DETAILED DESCRIPTION OF THE DRAWINGS

Figure 1:
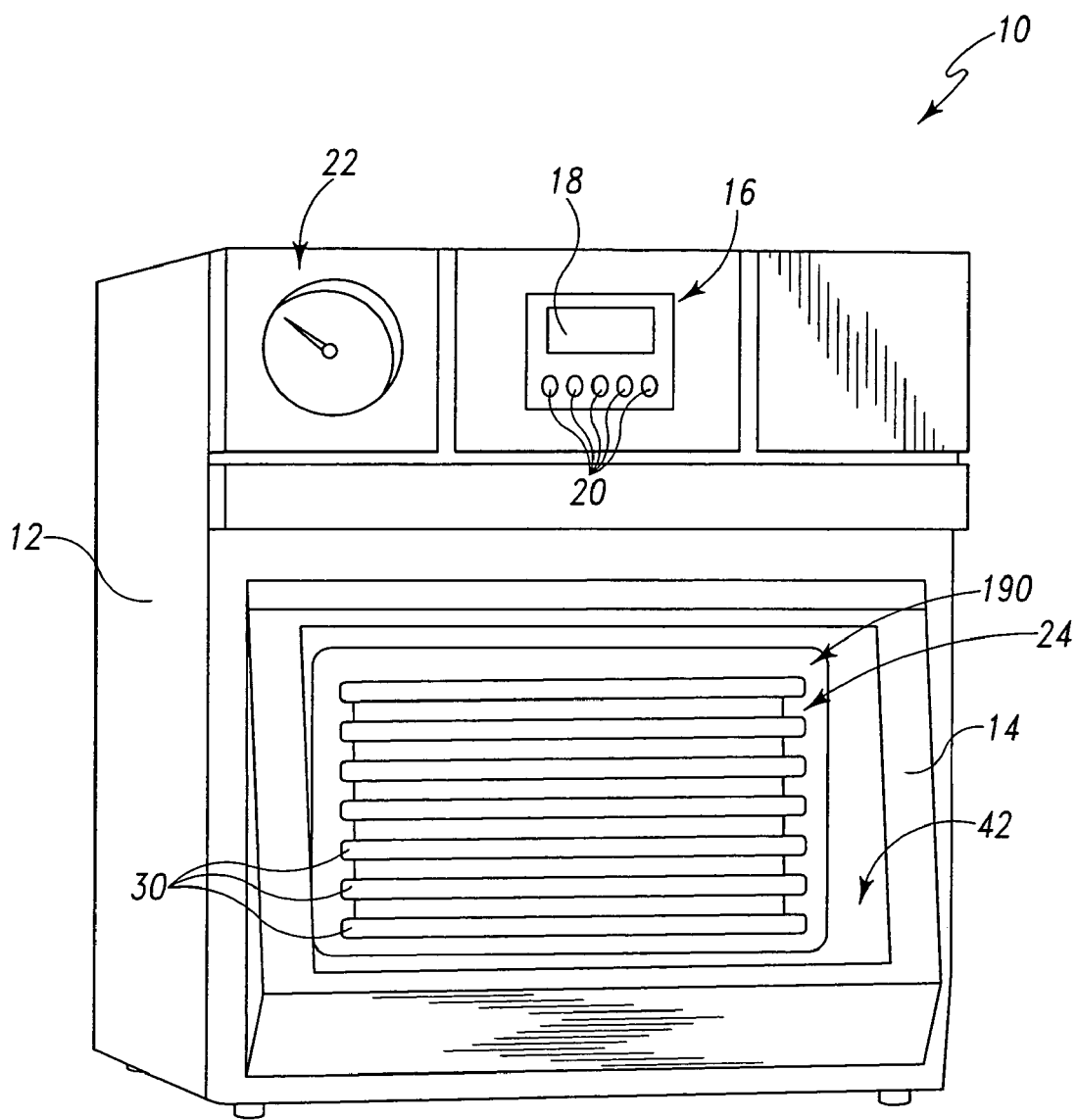
FIG. 1 is a perspective view of a platelet storage system having a platelet agitator located therein.
Figure 3:
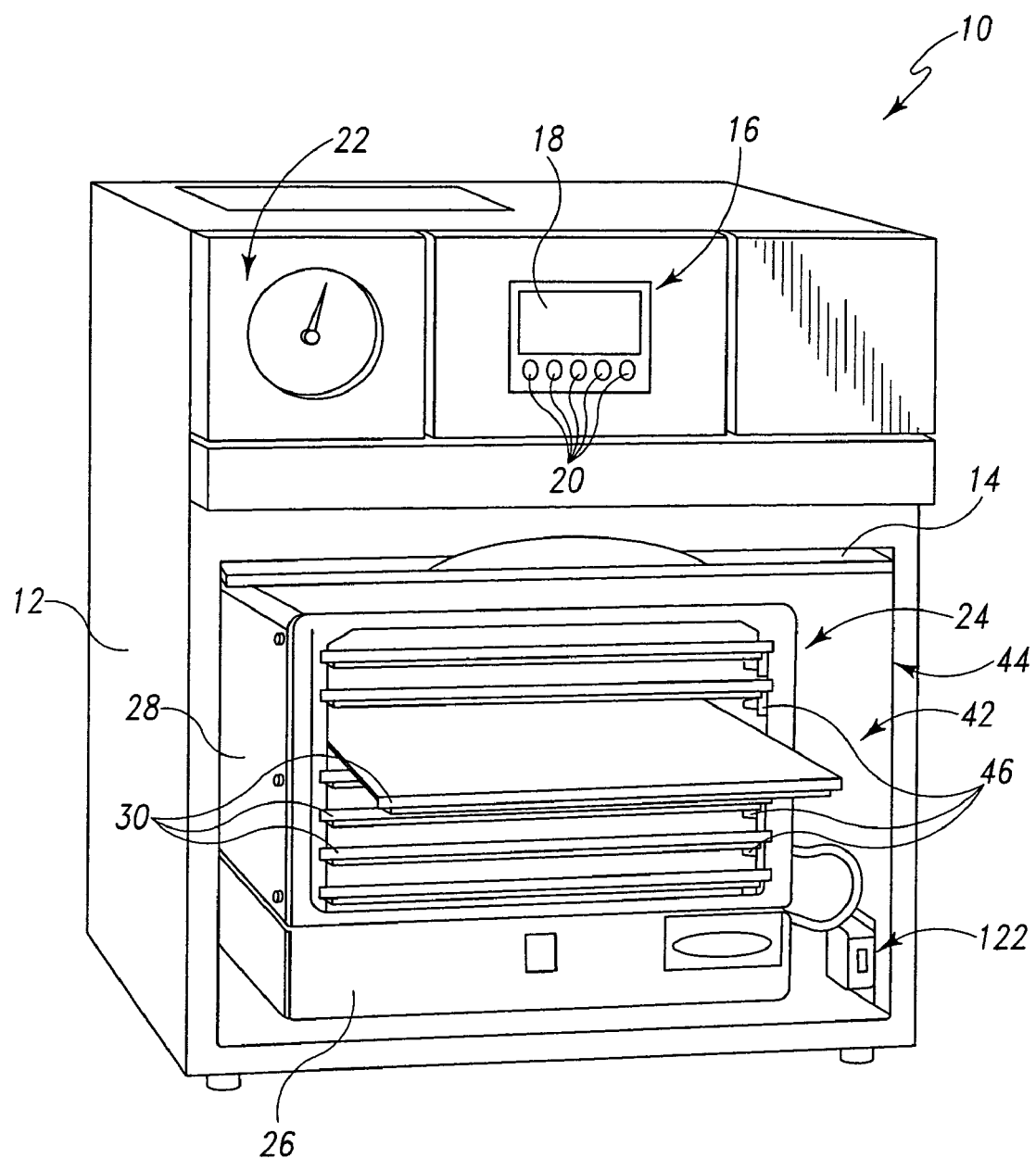
FIG. 3 is a perspective view of the platelet storage system of FIG. 1, with a door open and the agitator removed.

An incubator 10, used to preserve blood platelets, is shown in FIGS. 1 and 3. The incubator 10 has a cabinet 12 with an opening 44 to a storage compartment 42 therein. A door 14 is coupled to the cabinet 12 and is moveable between a closed position, wherein it covers the storage compartment 42 as shown in FIG. 1, and an open position as shown in FIG. 3. The door 14 has a sight opening 190 which permits a user to see through the door 14 into the storage compartment 42. The incubator 10 also has a controller 48 which located within the cabinet 12 and not seen. The controller 48 is part of a control system shown in FIG. 12 and described in further detail below. Referring to FIG. 3, a door switch 122 is coupled to the cabinet 12 and is in electrical communication with the controller 48 to provide a signal when the door 14 is closed.

Referring again to FIG. 1, a user interface device 16 coupled to the cabinet 12 includes a display device 18 and several input devices 20. The user interface device 16 is in communication with the controller 48 to provide inputs to the controller 48 a display outputs from the controller 48. The display device 18 is a monochromatic liquid crystal display (LCD). In some embodiments, the display device 18 may be a colored LCD display. In other embodiments, the display device 18 may be a touchscreen display with the input devices 20 integrated in the display. The input devices 20 of the illustrative embodiment of FIG. 1 are membrane switches. In some embodiments, the input devices 20 may be buttons. In addition, a audible output device 124 (seen diagrammatically in FIG. 12) is coupled to the cabinet 12 and in communication with the controller 48 to receive outputs from the controller 48 and synthesize sounds based on those outputs. The audible output device 124 is a piezoelectric device. In some embodiments, the sound device may be a speaker. In some embodiments, the sound device 124 may be coupled to the user interface device 16. In some embodiments, multiple sound output devices may be used.

Located inside of the storage compartment 42 is a temperature sensor 126 (shown diagrammatically in FIG. 12) which is in communication with the controller 48 and operable to provide a signal representative of the temperature inside of the storage compartment 42. The controller 48 is operable to process the temperature signal from the temperature sensor 126 to determine the actions necessary to control the temperature within the storage compartment 42. The temperature sensor 126 is also in communication with a temperature chart recorder 22 shown in FIG. 1 and described in detail below. In some embodiments, multiple temperature sensors 42 may be located throughout the storage compartment 42 with each temperature sensor 126 communicating an independent temperature to the controller 48 and controller 48 processing all of the temperature signals. The controller 48 controls a heating element 128 (shown diagrammatically in FIG. 12) located within the storage compartment 42 which is a resistive coil operable to provide heat to the storage compartment 42. In some embodiments, separate and independent temperature sensors 126 may be coupled to the temperature chart recorder 22 and the controller 48. In some embodiments, separate and temperature sensors 126 may be used to monitor and control the temperature within the storage compartment, one for monitoring and another for controlling.

Figure 12:
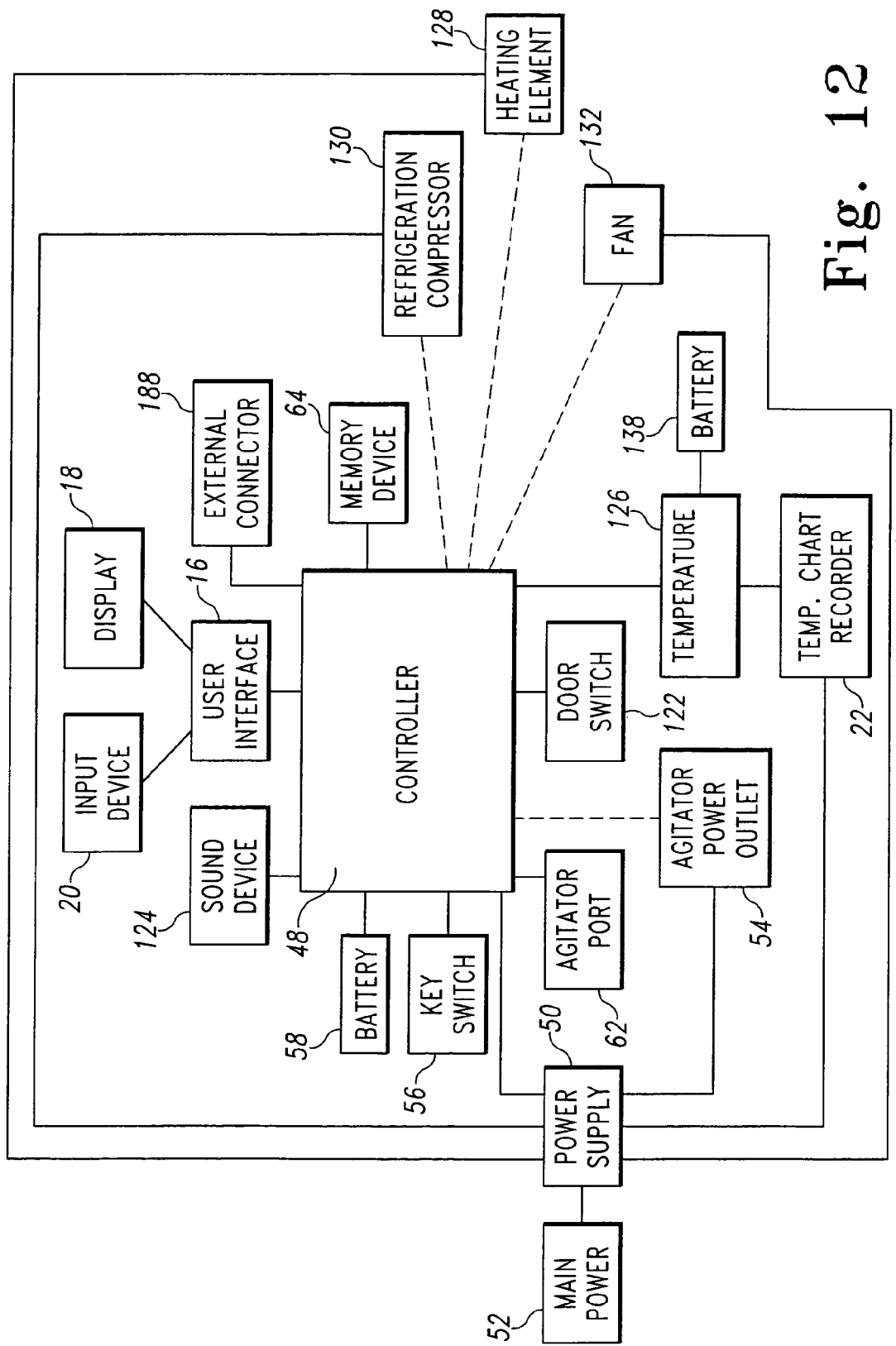
FIG. 12 is a diagrammatic view of the control system of the platelet storage system of FIG. 1.

Also located within the cabinet 12 and shown diagrammatically in FIG. 12 is a refrigeration compressor 130 which is coupled to the cabinet 12 cool the storage compartment 42. The refrigeration compressor 130 operates continuously. The heating element 128 is selectively operated so as to maintain a target temperature within the storage compartment 42. The heating element 128 includes an internal thermal protection device to prevent an over-temperature condition. In addition to the refrigeration compressor 130, there is a fan 132 which operates constantly so that the air within the incubator 10 is sufficiently dispersed to maintain a substantially constant temperature throughout the storage compartment 42. In some embodiments, there may be multiple fans 132

The controller 48 is a microprocessor based system which includes software to perform computations. The illustrative embodiment utilizes a proportional-plus-integral-plus-derivative (PID) control routine to operate the heating element 128. However, it should be understood that there are a number of feedback control schemes which may be utilized to control the temperature in the storage compartment 42. In some embodiments, the temperature sensor 126 used by the controller 48 to control the temperature within the storage compartment 42 may be different than the temperature sensor 126 used to monitor the alarms. The temperature sensor 126 is a thermocouple. However, it should be noted that any of a number of temperature sensors may be employed in determining the temperature within the storage compartment 42 and signaling the controller 48.

As shown in FIG. 12, the controller 48 is in communication with a memory device 134, which stores software used by the controller 48 and stores data related to the operation of the incubator 10 and a platelet agitator 24 which is located within the storage compartment 42 of the incubator 10 and in communication with the controller 48. The controller 48 is also in communication with an external connector 188 which permits a user to access the memory device 134 to update software or to download information stored by the controller 48.

Figure 2:
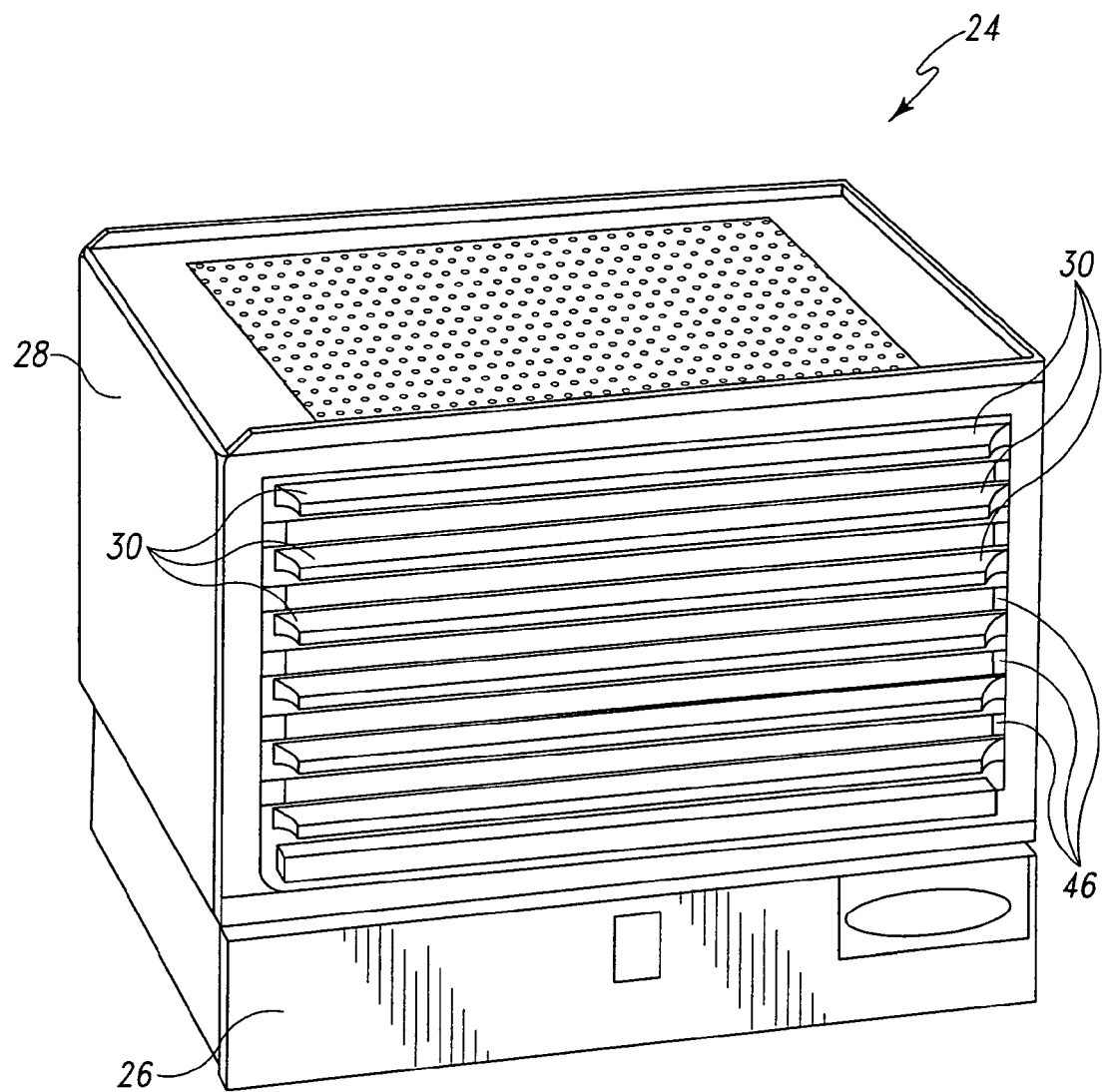
FIG. 2 is a perspective view of the platelet agitator of FIG. 1.

FIG. 1 shows the incubator 10 having the platelet agitator 24 located therein. FIG. 2 shows the agitator 24 separate from the incubator 10. As seen diagrammatically in FIG. 12, the agitator 24 is powered through an agitator power outlet 54 which is connected to the power supply 50 and is controlled by the controller 48. The agitator 24 communicates with the controller through the agitator port 62. Referring again to FIG. 2, the agitator 24 has a base 26, a frame 28, and several trays 30. The frame 28 has several rack members 46 which support the trays 30. The trays 30 slide on the rack members 46 so that platelet containers may be placed on the trays 30 and slid into the storage position as shown in FIGS. 1 and 2. FIG. 3 shows one of the trays 30 in an extended position so that the storage space of the tray 30 is accessible by a user.

Located within the base 26 but not visible is a motor and drive assembly which is operable to oscillate the frame 28 laterally in relation to the base 26. The motor is a single speed AC gear-motor with a speed monitor. The speed monitor, which is a proximity switch, is in communication with controller 48 and provides a signal to the controller 48 indicative of the speed of the motor. The proximity switch is operable to sense the frame 28 of the agitator 24 when the frame 28 moves laterally to a position near the proximity switch. When the frame 28 moves away from the proximity switch, the proximity switch ceases to sense the frame 28. The controller 48 is operable to process the signal from the proximity switch to determine the speed of the agitator 24 oscillations. A Hall effect proximity switch is used in the illustrative embodiment, however, it should be clear that other apparatuses may be used to monitor the speed of the oscillation of the frame 28. For example, in some embodiments, an rpm sensor is coupled directly to the motor output shaft. In other embodiments, a contact switch is used.

The controller 48 is operable to sense if the agitator 24 fails to oscillate. In such a case, the controller 48 begins a timing sequence based on a time interval input by a user. Once the time interval is reached, the controller 48 will alarm to inform a user that the oscillations have stopped and the controller 48 will log the alarm for future reference. In some embodiments, the controller 48 may be configured to allow a user to input upper and lower limits for speed so that the controller 48 will alarm if the speed exceeds or falls below the acceptable limits.

The motor output is pivotably connected to a crank arm which in turn is pivotably connected to the frame 28 of the agitator 24. The frame 28 is slides laterally relative to the base 26 on two slides (not shown). Each revolution of the gear-motor completes an agitation oscillation cycle by moving the frame 28 with respect to the base 26. This oscillation results in continuous agitation of the platelets, preventing the platelets from clotting.

Figure 4:
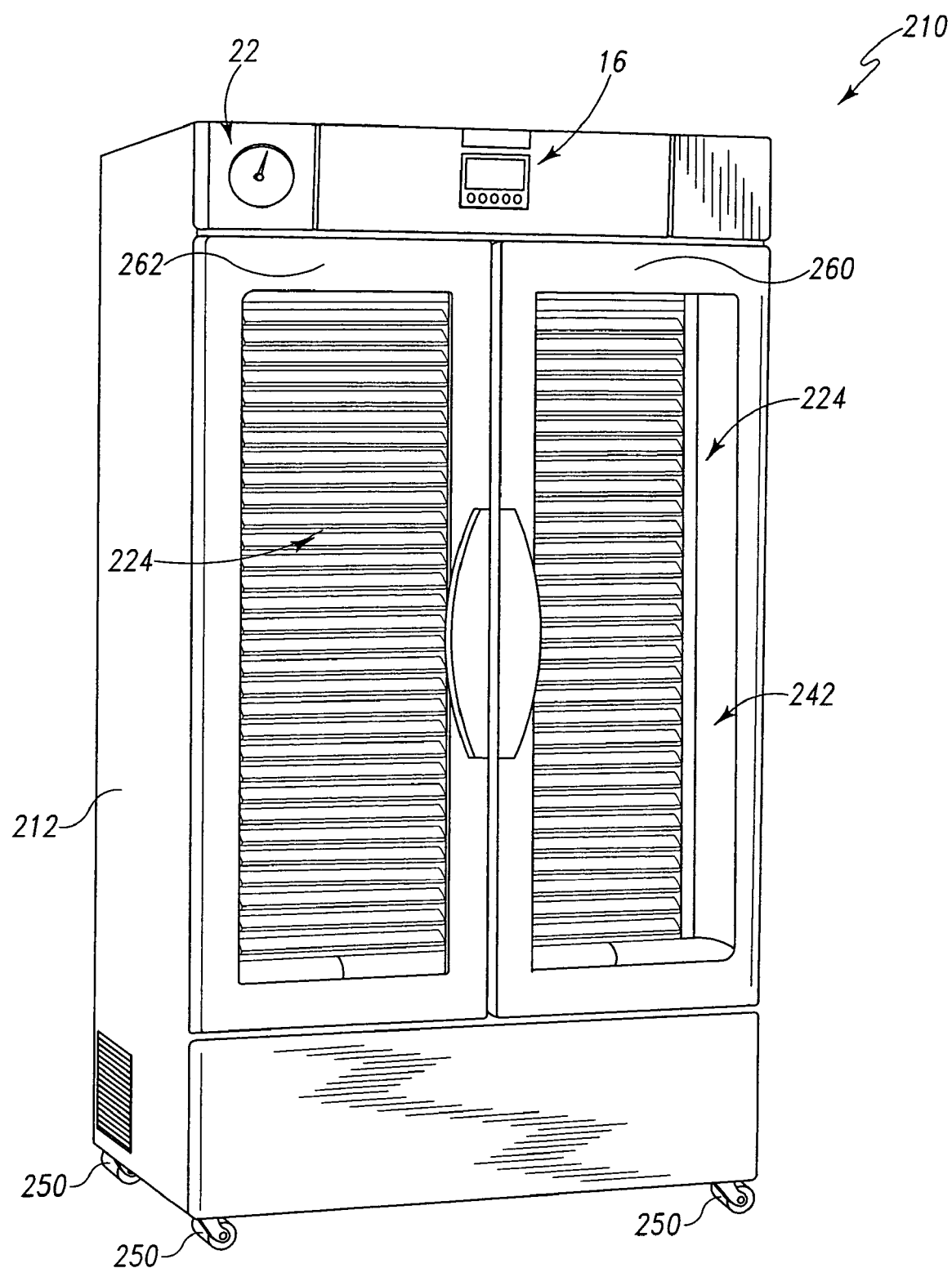
FIG. 4 is perspective view of another embodiment of a platelet storage system having a platelet agitator located therein.

FIG. 4 shows an alternative embodiment of the incubator 210 which is larger than the incubator 10 embodiment and has two larger agitators 224 placed in the storage compartment 242. The incubator 210 is mobile having casters 250 coupled to the bottom of a frame 212 of the incubator 210. In the illustrative embodiment of FIG. 4, the controller 48 receives signals from both agitators 224 and provides monitoring and alarms for each. The incubator 210 has two doors 260, 262 which open independently and have independent door switches 122 for each door to be monitored by the controller 48. In all other respects, the illustrative embodiment of FIG. 4 operates similarly to the illustrative embodiment of FIGS. 1-3.

Referring to FIG. 12, the relation of the controller 48 and other components of the apparatus are shown diagrammatically. The controller 48 receives power from a power supply 50 which conditions and controls power from a main power source 52. The main power source 52 is 110 volts AC. The power supply 50 converts the power as necessary and provides the proper voltage and current to the controller 48, an agitator power outlet 54, a temperature control unit 60, and a temperature chart recorder 22. The controller 48 is operable to turn the agitator power outlet 54 on and off as is represented by the dotted line connection between the controller 48 and agitator power outlet 54 in FIG. 12.

The controller 48 is also in communication with a key switch 56 as shown in FIG. 12. The key switch 56 is a mechanical switch that requires a key to actuate the switch between an on position and an off position. In the on position, the key switch 56 closes an electrical circuit which enables the controller 48 and incubator 10 to operate. When the key switch 56 is in the off position, the electrical circuit is open making the controller 48 and the incubator 10 inoperable.

Continuing to refer to FIG. 12, an agitator port 62 which is an electrical connection between the controller 48 and the agitator 24 which allows the agitator 24 to communicate to the controller 48 the agitator 24 speed in rpms and the total cycles the agitator 24 has completed. A single revolution of the motor results in a single cycle of oscillation of the agitator 24. The agitator 24 information is processed by the controller 24 and is accessible to a user through the user interface device 16 and is stored in a memory device 64 which is connected to the controller 48.

Figure 13:
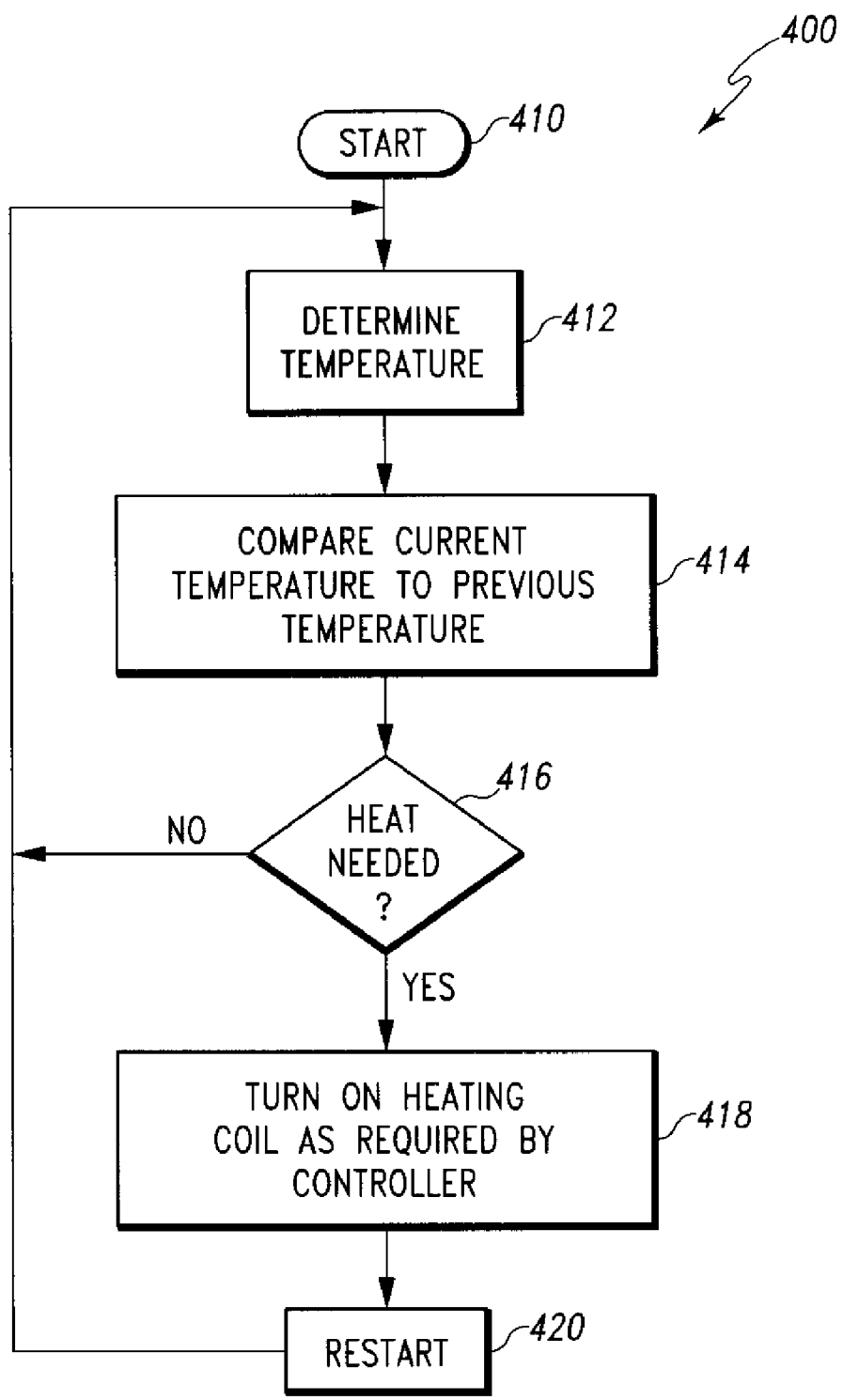
FIG. 13 is a flow chart of a control routine for control of the temperature within the incubator.

Referring now to FIG. 13, a control routine 400 for the control of the heating element 128 is shown. A step 410 in the routine represents the commencement step which occurs upon start-up of the incubator 10 and is followed by step 412 which determines the temperature of the storage compartment 42. The temperature is determined by the controller 48 which receives a signal from the temperature sensor 126, converts the signal from analog to digital, and processes the digital signal to convert it to a digital value indicative of the temperature in the storage compartment 42. Once the temperature value is determined, the control routine 400 progresses to step 414 where the current temperature value is compared to one or more previous temperature values. The temperature comparison is made considering the actual temperature value and the rate of change of temperature in the storage compartment 42.

In step 414, a proportional-plus-integral-plus-derivative (PID) based control routine is used to make a branch decision whether or not to turn on the heating element 128. The PID control routine may be adapted to consider temperature rises and decays within the storage compartment. Moreover, the effect of additional heat created by the heating element 128 even after the unit is turned off may be considered in the step 414.

At step 416, the control routine 400 makes the determination as to whether heating is necessary. If no heating is necessary, the routine 400 cycles back to step 412 and repeats the process. If heating is necessary, then the routine 400 progresses to step 418 and turns the heating element 128 on for a predetermined period of time. Once the step 418 is complete, the routine progresses to step 420 which restarts the analysis at the step 412 and completes another loop of the control routine 400.

Figure 14:
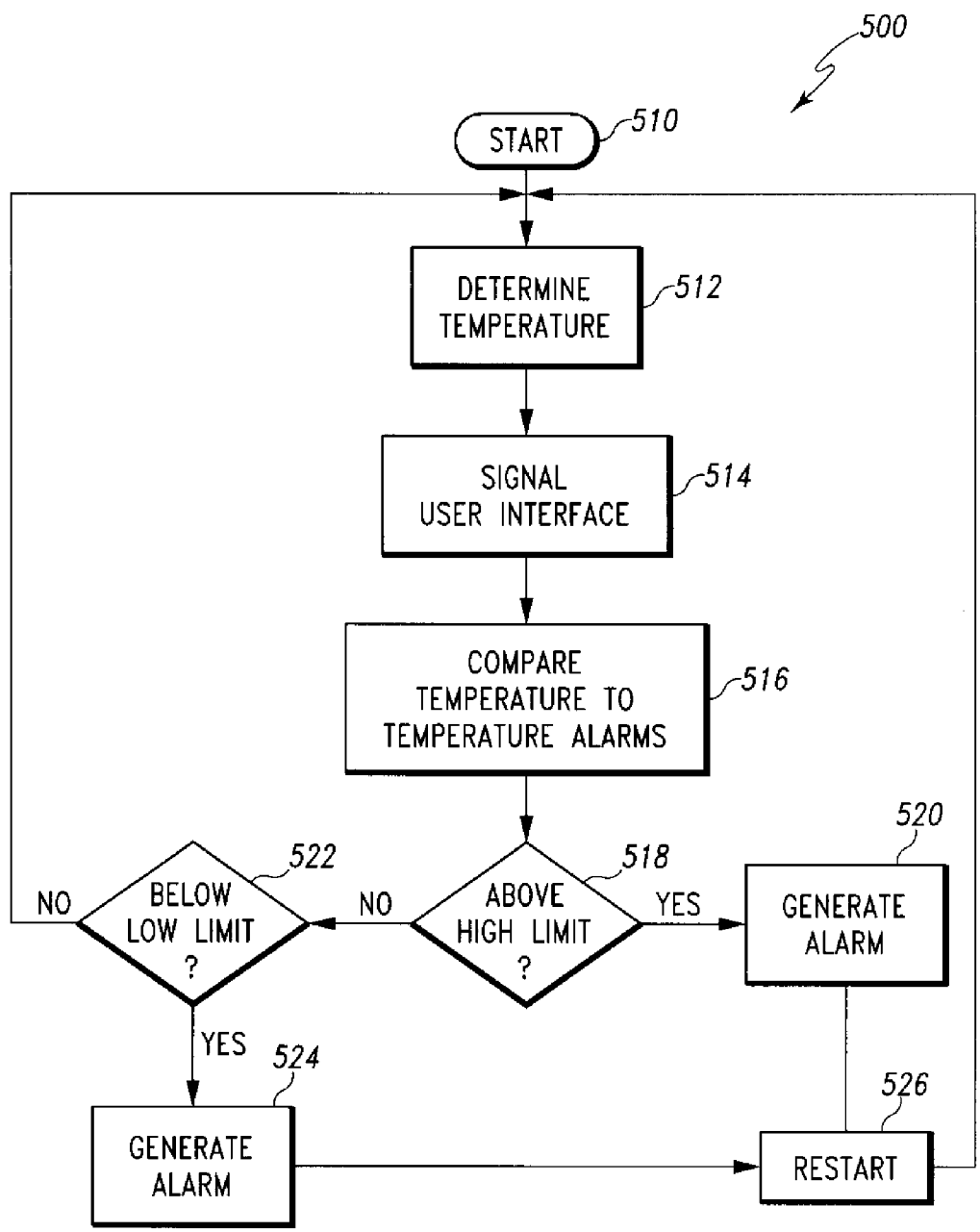
FIG. 14 is a flow chart of a control routine for the monitoring and displaying of the temperature and temperature alarms for the incubator.

A control routine 500, shown in FIG. 14, operates continuously during operation of the incubator 10 to monitor the temperature in the storage compartment 42 and compare the temperature in storage compartment 42 to the alarm limits set by a user. The control routine 500 commences at start-up of the incubator 10 at step 510. The control routine 500 then advances to step 512 where the temperature is determined by the controller 48 which receives a signal from the temperature sensor 126, converts the signal from analog to digital, and processes the digital signal indicative of the temperature in the storage compartment 42. Once the temperature is determined, the controller 48 progresses to step 514 where the value of the temperature is passed to the user interface device 16 as a digital signal which is then converted by the user interface device 16 to create a numeric representation of the temperature on the display device 18.

The control routine then progresses to step 516 where the temperature is compared to the alarms set by the user. At step 518, the control routine 500 evaluates the temperature to the high limit. If the temperature is above the high limit, the control routine 500 advances to step 520 where a high temperature alarm is generated. Generation of the high temperature alarm results in a signal to the display device 18 of the user interface device 16 which provides a visual indication of the alarm. Additionally, the audible output device 124 is signaled to generate an audible alarm and the alarm is logged by the control routine 700 discussed below. The control routine 500 then progresses to step 526 which results in a restart of the control routine 500.

If the determination at 518 is that the temperature level is not above the high limit, then the control routine 500 advances to step 522 which compares the temperature to the low limit. If the temperature is below the low limit, the control routine is advanced to step 524 which results in the generation of an alarm similar to step 520 discussed above. Namely, a visual alarm is signaled to the display device 18, an audible alarm is signaled to the sound device 124, and the alarm will be logged by control routine 700. Once the alarm has been generated, the control routine advances to step 526 which results in a restart of the control routine 500. In the event that the temperature is not below the low limit at step 522, then the control routine returns to step 512 to complete another iteration of the control routine 500. Control routine 500 thereby continuously monitors the temperature and temperature alarm status during the operation of the incubator 10.

Figure 15:
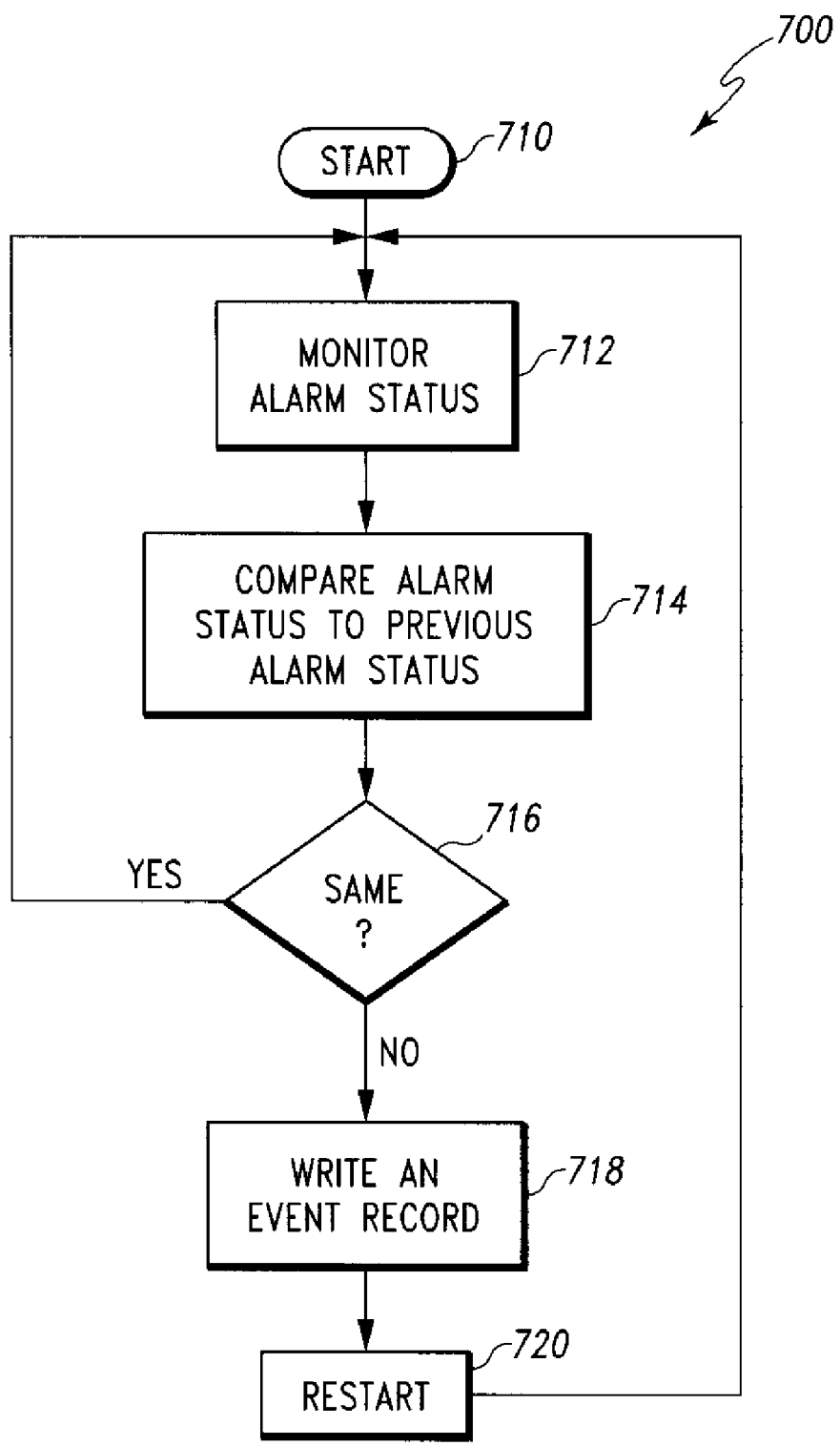
FIG. 15 is a flow chart of a control routine for the monitoring, displaying, and logging of alarms associated with the operation of the incubator.

An event log control routine 700 is shown in FIG. 15. The purpose of the event log control routine 700 is to provide a detailed history of the alarms experienced by the incubator 10 so that a user may evaluate the operation of the incubator 10 and determine if the incubator 10 is operating properly and safely preserving the blood products stored therein. The event log control routine 700 commences at step 710 upon start-up of the incubator 10 and advances to step 712 where the current status of all alarms within the incubator 10 is determined.

The control routine 700 then advances to step 714 where the alarm statuses are compared to the previous alarm statuses in the previous loop. At step 716, a branch decision is made. If the alarm statuses are the same, the control loop 700 returns to step 712 to complete another loop of the control routine 700. If the alarm statuses are not the same, then the control routine 700 advances to step 718 which results in an event record being generated and written to memory. The event record includes a serial identifier, a status identifier, namely, whether it is the beginning or ending of the event, the date of the event status logged, the time of the event status logged, the temperature within the storage compartment 42 at the time of the log entry, and a code identifying the type of event. Types of events logged include door open, high storage compartment temperature, low storage compartment temperature, high refrigeration compressor temperature, low battery, no battery, mains power failure, and agitator failure. The control routine 700 operates continuously during the operation of the incubator 10 such that the event log includes all events which occur.

FIGS. 5-7 show screens associated with the operation of the incubator 10. FIG. 5 shows a home screen which is a status screen. The home designator 134 in the upper left hand corner of the display device 18 informs a user that the home screen is active. A battery status indicator 136 displays the approximate life of a back-up battery 138 which is available to power a temperature chart recorder 22 as seen in FIG. 1. The current date 140 and time 142 are also displayed on the home screen.

The home screen of FIG. 5 also displays the current temperature 144 in the incubator 10 as sensed by the temperature sensor 126 and processed by the controller 48. Additionally, a graph 146 shows a line 148 representing the temperature over the previous 24 hours. The graph 146 also includes a line 150 and text 152 indicating the upper limit of the temperature. Similarly, the graph 146 includes a line 154 and text 156 indicating the lower limit of the temperature. These limits are established by a user in configuring the operation of the incubator 10.

Activating any of the input devices 20 when the home screen is displayed, as shown in FIG. 5, results in the display moving to a main screen as shown in FIG. 6. The main screen is identified by a home screen designator 158. Also shown on display device 18 is a menu list 160 of activities and information that can be accessed by the user. The menu selections include review of the event log, review of the system alarms test and status, edit configuration, view configuration, a product/company information section, and online help. On the lower part of the display device 18, text designators of navigation operations are displayed above associated input devices 20. Activation of the associated input device 20 results in the navigation operation being performed. For example, activation of the input device 20 associated with the home designator 96 will result in returning to the home screen shown in FIG. 5. Activation of the input device 20 associated with the up designator 100 will move a cursor to the selection above the highlighted selection in the menu list 160. The event log 162 menu choice is highlighted in FIG. 6. Activation of the down designator 110 will result in the highlighting moving to the next menu list 160 choice, system alarm test & status 164. Utilizing the up 100 and down 110 operations, a user can move through the selections on the menu list 160. Once the correct menu list 160 selection is highlighted, activation of the input device 20 associated with the select designator 166 will result in navigation to another screen associated with that menu selection.

An example of one of the screens that may be accessed from the main screen shown in FIG. 6 is the set alarm set points screen shown in FIG. 7. The set alarm set points screen designator 168 identifies the screen purpose for the user. In this particular screen, the user has the ability to adjust the alarms for high alarm set point 170, door ajar timeout 172, and power failure timeout 174. As shown in FIG. 7, the high alarm set point 170 item is highlighted. This particular alarm is associated with the temperature and establishes the value at which the high temperature alarm will be activated. If the user input device 20 associated with an increase designator 176 is activated, the value of the set point for the alarm is increased. Likewise, if the user input device 20 associated with a decrease designator 178 is activated, the set point for the alarm is decreased.

The door ajar timeout 172 and power failure timeout 174 are adjusted in a similar manner. The door ajar timeout 172 set point is the time in minutes that the door 14 is allowed to remain open before an alarm is triggered to let a user know that the door 14 is open. Similarly, the power failure timeout 174 set point is the time in minutes that the incubator 10 is permitted to be without power before an alarm is triggered. Once the set points have been adjusted, the user may return to the previous screen by activating the user input device 20 associated with the back designator 196 to return to a previous screen. The activation of the input device 20 associated with the home designator 96 will return the display to the home screen as shown in FIG. 5.

While the illustrative screens of FIGS. 5-7 show various displays and navigation that are representative of the present invention, it should be understood that a number of similar screens may be accessible. For example, alarms for the low temperature or temperature at the refrigeration compressor may be set. Likewise, screens which provide for product configuration may be accessible. Configuration may include identifying various accessories to the incubator 10, calibration of temperature sensor, management of passwords, resetting of factory default configuration, or similar operations. In addition, help screens may be available to provide information related to preventative maintenance, product information, manufacturer information, service telephone numbers and the like may also be accessible through the user interface.

Figure 8:
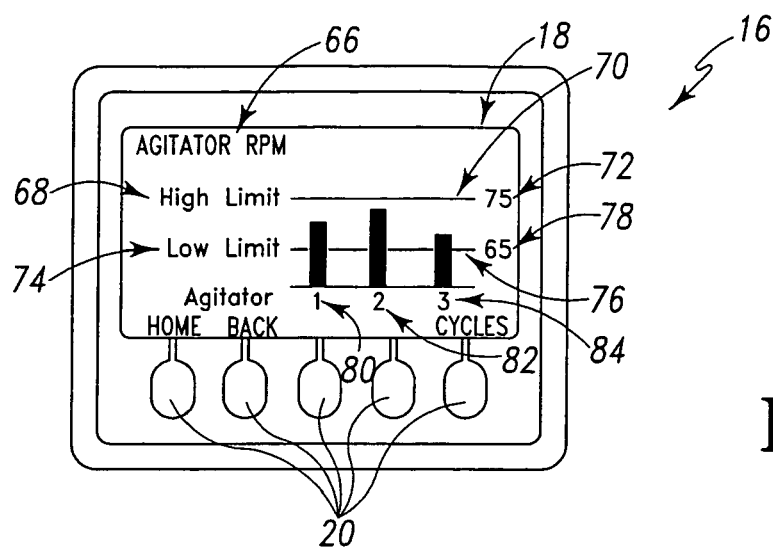
FIG. 8 is a perspective view of the user interface of FIG. 5, the display screen displaying an agitator status screen.
Figure 9:
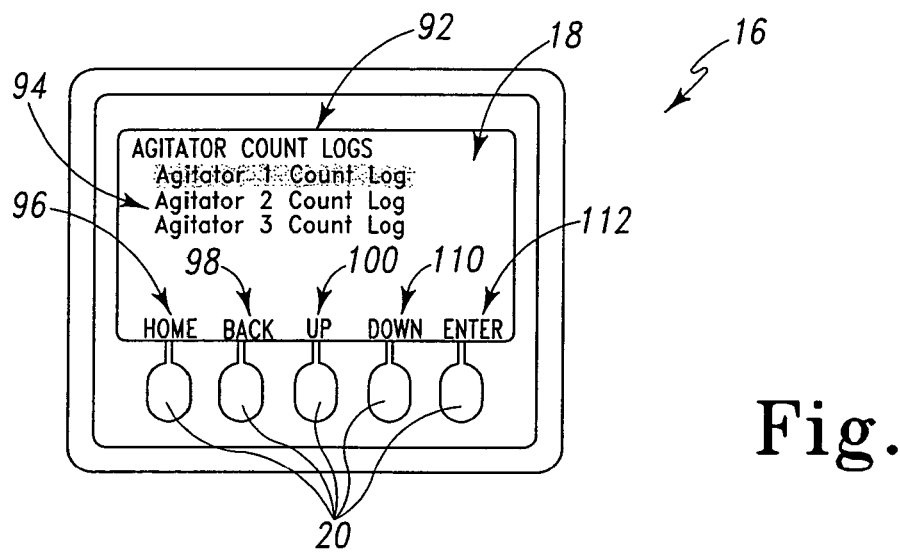
FIG. 9 is a perspective view of the user interface of FIG. 5, the display screen displaying a menu screen for agitator count logs.
Figure 10:
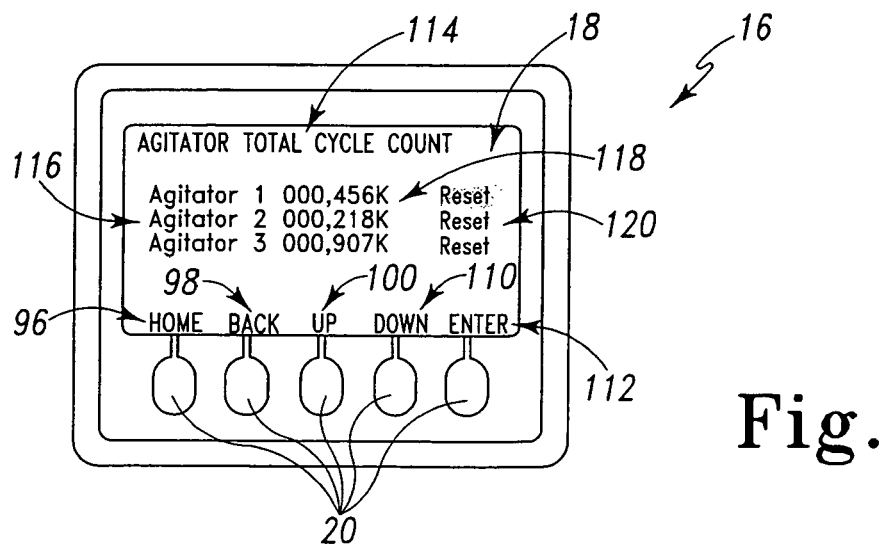
FIG. 10 is a perspective view of the user interface of FIG. 5, the display screen displaying cycle counts for various agitators.

FIGS. 8-10 show various information related to the operation of agitators 24. FIG. 8 shows the display device 18 displaying the speed of three agitators 24 connected to the incubator 10. The agitator rpm screen designator 66 gives the user an indication of the information being displayed. The high limit for the speed is designated by text 68, a line 70, and a numerical value 72. Likewise, the low limit for speed is designated by text 74, a line 76, and a numerical value 78. Agitator 24 speed being reviewed is designated numerically by designators, with a designator 80 corresponding to the first agitator, a designator 82 corresponding to the second agitator, and a designator 84 corresponding to the third agitator. A graphical representation of the speed of each of the agitators 24 is provided in the form of a bar graph. In FIG. 8, the first bar 86 corresponds to the speed of the first agitator, the bar 88 corresponds to the speed of the second agitator, and the bar 90 corresponds to the third agitator.

Referring now to FIG. 9, the display device 18 shows a navigation screen for information related to agitators 24. An agitator count logs screen designator 92 shows the screen name. Access to the count logs for three different agitators is displayed on the screen. The Agitator 1 Count Log selection 94 is highlighted. Several navigation designators are located on the bottom part of the display device 18 with each designator being associated with one of the input devices 20. The designators include a home 96, a back 98, an up 100, a down 110, and an enter 112. In FIG. 9, activation of the input device 20 associated with the enter 112 designator would result in moving to the next screen associated with the highlighted Agitator 1 Count Log selection 94.

A summary of agitator cycles is provided in the screen shown in FIG. 10. The agitator total cycle count screen designator 114 shows the screen name as a reference to a user. The display device 18 also shows the total cycles for each of three agitators 24 attached to the incubator. Each line displayed shows an agitator number and the cycles for that agitator. For example, the line for agitator 2 has a text designator 116 and a cycle count value 118. Also associated with the line for agitator 2 is a reset designator 120. The reset designator 120 allows a user to reset the cycle count to zero for the agitator 24 of the associated reset designator 120. This screen 114 has the same navigation designators of FIG. 9 and operates in the same manner.

Figure 11:
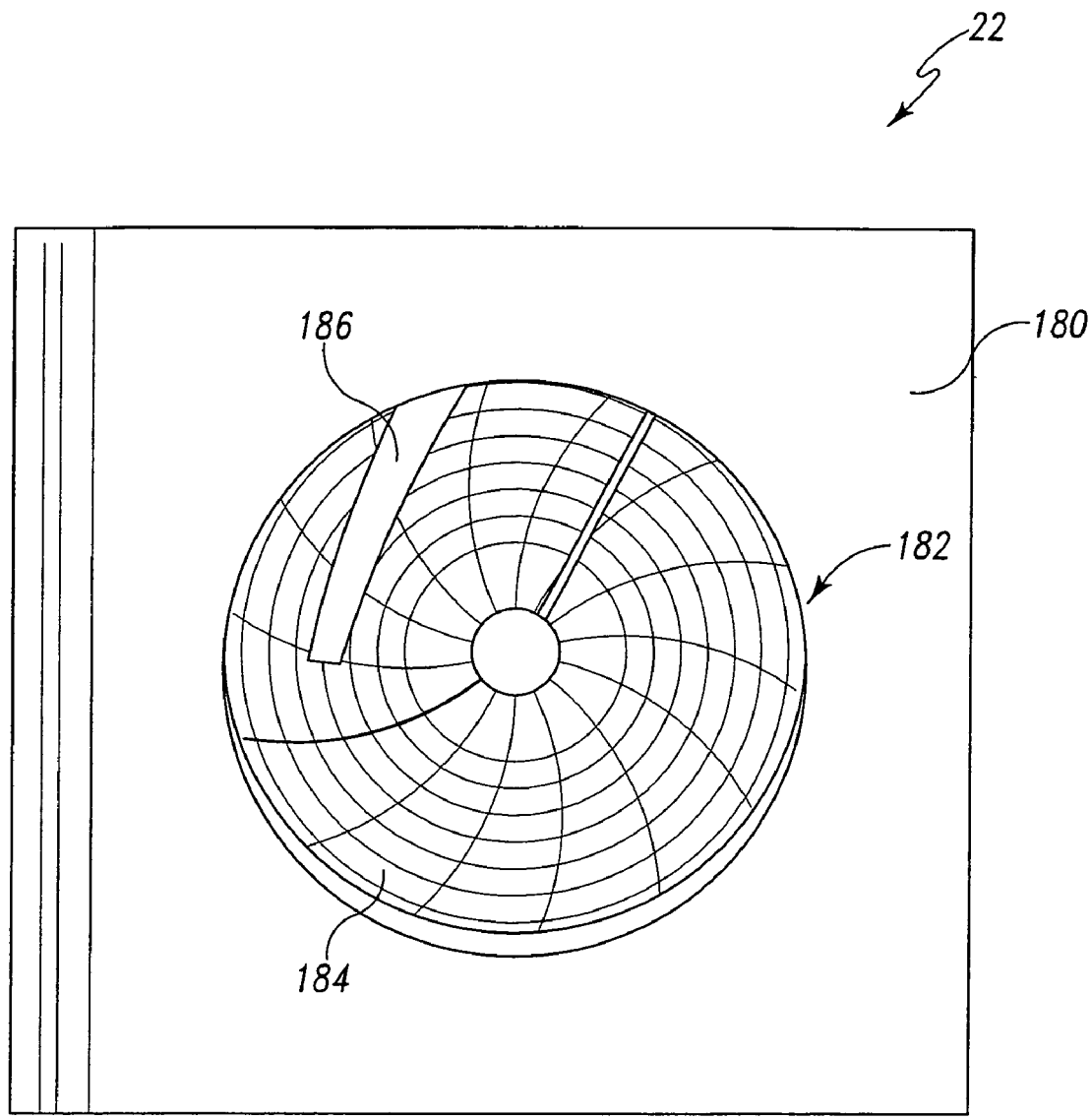
FIG. 11 is a perspective view of a mechanical temperature chart recorder of the platelet storage system of FIG. 1.

The temperature chart recorder 22 is shown in FIG. 11. This temperature chart recorder 22 is similar to other laboratory chart recorders. The recorder 22 is behind a door 180 having a clear opening 182 which permits a user to view the recorded temperature. The temperature is recorded on chart paper 184. A stylus 186 has a marking pen (not shown) which marks the chart paper 184. Over time, the chart paper 184 is rotated and the stylus is moved to trace the temperature in the storage compartment 42 over a seven day period. As shown in FIG. 12, the temperature chart recorder 22 is connected to a battery 138 which provides power to the recorder 22 in the event that power to the recorder 22.

In operation, the incubator 10 is used to store bags of platelet material which are placed on the trays 30. A user will regularly open the door 14 to access the trays 30, placing bags on the trays 30 or removing the bags. Each time the door 14 is opened, the controller 48 will sense the opened door 14 and log an event indicating the door 14 has been opened. The log of the event will include the information discussed above and will be stored in the memory device 64. Additionally, the incubator 10 controller 48 will continuously to operate the refrigeration compressor 130 and the fan 132 while monitoring the temperature sensed by the temperature sensor 126. As required to maintain the temperature within the storage compartment 42, the controller 48 will activate the heating element 128 in the storage compartment 42. While continuously monitoring the temperature, the controller 48 will store the temperature at preset intervals to be displayed on the display device 18 of the user interface device 16. If the temperature falls outside of the preset set points for low and high temperature, the controller 48 will signal an alarm through the user interface device 16 display device 18 and the audible output device 124.

In addition, the controller 48 will continue to signal the agitator 24 to operate while simultaneously monitoring the output from the rpm sensor coupled to the drive in the agitator 24. If the agitator 24 fails to oscillate, the controller 48 will provide an alarm as described above.

The result is that the incubator 10 and agitator 24 are monitored with a configurable alarm system and data associated with the alarms is logged to be accessible by a user. This combination provides the user with the ability to monitor and review the operation of the incubator 10 and agitator 24 to assure proper storage of blood platelets.

Although certain illustrative embodiments have been described in detail above, variations and modifications exist within the scope and spirit of this disclosure as described and as defined in the following claims.

The invention claimed is:

1. An incubator for storage of blood platelets, the incubator comprising:
   a storage cabinet defining a storage space and a door moveable between an open position and a closed position,
   a heating element positioned in the storage space,
   a refrigeration unit positioned in the storage space,
   a controller electrically coupled to the heating element and refrigeration unit,
   a temperature sensor electrically coupled to the controller,
   an agitator positioned in the storage space, the agitator including a base and a frame which oscillates linearly relative to the base, and
   a user interface in communication with the controller and configured to receive inputs from a user and display outputs from the controller.

2. The incubator of claim 1, wherein: the controller is configured to store a log of events, and the display is configured to display the log events.

3. The incubator of claim 2, wherein: the log includes the date of the event, the time of the event, and the sensed temperature within the storage space during the event.

4. A platelet incubator, comprising:
   a storage cabinet defining a storage space, the cabinet including a door movable between an open position permitting access to the storage space and a closed position,
   a controller,
   a memory device in communication with the controller,
   a user input device in communication with the controller operable to receive input from a user,
   a display device in communication with controller operable to display output from the controller,
   a temperature sensor in communication with the controller operable to sense the temperature of the storage cabinet,
   an agitator positioned in the storage space, the agitator including a base and a frame which oscillates linearly relative to the base, and
   a heating element in communication with the controller operable to be activated by the controller and heat the storage cabinet.

5. The platelet incubator of claim 4, wherein: the controller comprises a microprocessor and the memory device includes instructions that, when executed by the microprocessor, cause the controller to control the temperature in the storage space.

6. The platelet incubator of claim 5, wherein: the microprocessor uses a feedback control system to control the heating element.

7. The platelet incubator of claim 6, wherein: the feedback control system is a proportional-plus-integral-plus-derivative controller.

8. The platelet incubator of claim 4, wherein: the heating element includes a thermal protection device to prevent the heating element from overheating.

9. The incubator of claim 4, wherein: the control system is configured to log events that are known to effect the temperature of the storage cabinet, the log stored in the memory device.

10. The incubator of claim 9, wherein: the information stored in the log includes the date of the event, the time of the event, and the temperature within the storage space.

11. The incubator of claim 3, wherein: an event is logged if the agitator frame fails to oscillate at an acceptable speed relative to the agitator base.

12. The incubator of claim 1, wherein: the controller is configured to monitor and control the oscillation speed of the agitator frame relative to the agitator base.

13. The incubator of claim 12, wherein: the agitator is oscillated at a rate that is sufficient to prevent coagulation of platelets stored in the incubator.

14. The incubator of claim 4, wherein: the agitator includes a sensor in communication with the controller and the controller monitors the speed of oscillation of the frame of the agitator relative to the base of the agitator.

15. The incubator of claim 5, wherein: the memory device includes instructions that, when executed by the microprocessor, cause the controller to monitor the temperature in the storage cabinet and monitor the speed of oscillation of the frame of the agitator relative to the base of the agitator.

16. The incubator of claim 15, wherein: a user may input at least one alarm condition for an operational parameter and the controller logs an event if the alarm condition is met.

17. The incubator of claim 16, wherein: a user may input an alarm condition for the temperature sensed by the temperature sensor or the speed of oscillation of the agitator frame relative to the agitator base.

18. The incubator of claim 17, wherein: the information stored in the event log includes the date of the event, the time of the event, and the temperature within the storage cabinet.

19. The incubator of claim 4, wherein: the controller creates an event log and an event is logged if the door of the storage cabinet is opened.

20. The incubator of claim 19, wherein: the information stored in the event log includes the date of the event, the time of the event, and the temperature within the storage cabinet.

* * * * *